United States Patent [19]

Roszinski et al.

[11] 4,020,129
[45] Apr. 26, 1977

[54] PRODUCTION OF DITHIOPHOSPHORIC ACID-O,O-DIESTERS

[75] Inventors: Hilmar Roszinski; Bernd Lippsmeier, both of Hurth-Knapsack; Gerhard Hartlapp, Hurth-Hermulheim, all of Germany

[73] Assignee: Hoechst Aktiengesellschaft, Frankfurt am Main, Germany

[22] Filed: Apr. 29, 1975

[21] Appl. No.: 572,838

[30] Foreign Application Priority Data

May 3, 1974 Germany .......................... 2421462

[52] U.S. Cl. ................................ 260/983; 260/963
[51] Int. Cl.² .................... C07F 9/17; C07F 9/173; C07F 9/18; C07F 9/177
[58] Field of Search ............................ 260/983, 987

[56] References Cited

UNITED STATES PATENTS

| | | | |
|---|---|---|---|
| 2,710,269 | 6/1955 | Higgins et al. | 260/983 X |
| 3,671,612 | 6/1972 | Roszinski et al. | 260/987 X |
| 3,717,692 | 2/1973 | Roszinski et al. | 260/987 X |

OTHER PUBLICATIONS

Mastin et al., Journal of the American Chemical Society, vol. 67 (1945) pp. 1662 to 1664.

*Primary Examiner*—Richard L. Raymond
*Attorney, Agent, or Firm*—Connolly and Hutz

[57] ABSTRACT

Production of pure dithiophosphoric acid O,O-diesters of the general formula

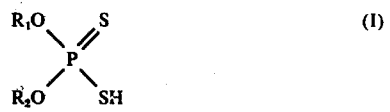
(I)

in which the radicals $R_1$ and $R_2$, being identical or different, each stand for linear and/or branched alkyl, cycloalkyl, alkenyl, alkinyl, aralkyl or aryl radicals having from 1 to 18 carbon atoms, from their salts of the general formula:

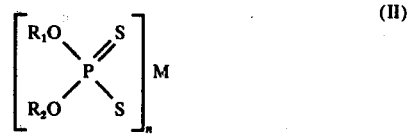

(II)

in which $R_1$ and $R_2$, respectively, have the meanings given hereinabove, M stands for a metal or ammonium cation, and $n$ stands for the valency of the particular cation. The compounds are made by dissolving the salts in the quantity of one or more strong acids necessary to ensure reaction with the resultant formation of two separate liquid phases, and separating the two phases from one another.

8 Claims, No Drawings

PRODUCTION OF DITHIOPHOSPHORIC ACID-O,O-DIESTERS

The present invention relates to a process for recovering pure dithiophosphoric acid O,O-diesters of the general formula:

in which the radicals $R_1$ and $R_2$, being identical or different, each stand for linear and/or branched alkyl, cycloalkyl, alkenyl, alkinyl, aralkyl or aryl radicals having from 1 to 18 carbon atoms, preferably from 1 to 6 carbon atoms, more preferably from 1 to 4 carbon atoms, from their salts of the general formula:

in which $R_1$ and $R_2$, respectively, have the meanings given hereinabove, M stands for a metal or ammonium cation, and $n$ stands for the valency of the particular cation concerned.

It has long been known that dithiophosphoric acid O,O-diesters can be made by reacting phosphorus sulfides with alcohols or phenols (Houben-Weyl, Methoden der org. Chemie, Georg Thieme Verlag, Stuttgart, volume XII/2, page 684 et. seq. (1964)). The products so made are more less contaminated with various by-products, irrespective of whether they are made in the presence or absence of a solvent or diluent, and irrespective of the particular alcohol or phosphorus sulfide used. The reaction of $P_4S_{10}$ with methanol, for example, has been found to yield a product containing not more than between about 85 and 90% of dithiophosphoric acid O,O-dimethylester. The reaction product contains, for example, thiophosphorous acid-O,O-dimethylester, dithiophosphoric acid-O,O,S-trimethylester and thiophosphoric acid-O,O,O-trimethylester together with further contaminants, which can in fact, be removed therefrom, however at the price of very expensive purifying or separating treatment, if at all. The low thermal stability of dithiophosporic acid O,O-diesters makes it substantially impossible for them to be purified under technically attractive conditions, for example by distillation under vacuum. This is applicable, if at all, to the lower dithiophosphoric acid-O,O-dimethylester up to the dithiophosphoric acid O,O-dipropylester. Despite this, the yields are not higher than 80-85%. It should be added that ill-smelling distillation residues are obtained, which are difficult to handle and have to be disposed of by very expensive antipollutive technology.

A generally applicable method for purifying crude dithiophosphoric acid-O,O-diesters by wet-processing treatment, e.g. with sodium carbonate, aqueous hydrochloric acid and ether, has been described by W. E. Bacon and W. M. de Suer in J. Amer. Chem. Soc. 76, 670 (1964), which, however, calls for considerable expenditure of energy and chemicals. Such purification is not very suitable for use in commercial processes.

It is widely known that compounds of the formula $(RO)_2P(S)SH$ can be obtained from trithiometaphosphoric acid esters (cf. L. Rosnati, Gazzetta Chimica Italiana, 76, 272 (1946)). Dithiophosphoric acid-O,O-diarylesters are, however, substantially the only compounds obtainable in this manner and in very moderate yields. In addition to this, the dithiophosphoric acids so made are more or less strongly contaminated and it is necessary for them to be purified later.

The present invention now unexpectedly provides a process permitting pure high-grade dithiophosphoric acid-O,O-diesters of the general formula (I) to be produced in simple manner from their salts of general formula (II), which comprises dissolving the salts in the quantity of one or more strong acids necessary to ensure reaction with the resultant formation of two separate liquid phases and separating the two phases from one another.

The process should preferably be effected with the use of strong mineral acids, more preferably with sulfuric acid or phosphoric acid.

It is also advantageous for the above process to be effected at temperatures within the range −5° and +60° C, preferably within the range 0° and 30° C, so as to avoid thermal decomposition reactions.

The use of acids containing the quantity of water necessary to ensure dissolution of the particular dithiophosphate used has been found very advantageous. It is accordingly good practice to use acids having a strength within the range 30 and 90 weight %, preferably within the range 65 and 85 weight %.

The acid may advantageously be used in an excess, based on the quantity theoretically needed.

The dithiophosphate of formula (II) and the acid may preferably be used in a quantitative ratio of more than 1 : 12, more preferably in a ratio within the range 1 : 5 and 1 : 1.

Particularly useful starting materials are the alkali metal or ammonium salts of dithiophosphoric acid-O,O-diesters.

The use of phosphoric acid of 65-85% strength or of sulfuric acid entails a further beneficial effect. In this case, the reaction mixture undergoes a temperature drop during the reaction, making decomposition of dithiophosphoric acid-O,O-diesters practically impossible. As a result, very pure products are obtained in substantially The compounds of general formula (II) which may be used in the process of the present invention, include practically all metal or ammonium-O,O-dithiophosphates capable of reacting with strong acids under the conditions of the present process, the alkali metal and ammonium salts being preferred.

Very useful starting materials are, for example, the ammonium-O,O-dialkyldithiophosphates described in German Patent Specification 1,768,151.

As reported above, the present process is easy to carry out and unhazardous and accordingly very well adapted for use on a commercial scale. The salt solutions, which are obtained if phosphoric acid or sulfuric acid is used, can readily be used for making fertilizers or commercial salts. In other words, it is possible for the present process to be carried out under ecologically beneficial conditions.

The high-grade dithiophosphoric acid-O,O-diesters obtainable by the present process are interesting starting materials for making insecticides and pesticides.

EXAMPLE 1

280 g of ammonium-O,O-dimethyl-dithiophosphate was added within 15 minutes with thorough agitation to 800 g of 75% phosphoric acid. During the addition, the temperature dropped from 24° C down to 9° C. After a reaction period of 25 minutes, the reaction mixture was delivered to a separating vessel. It was allowed to remain therein for 20 minutes and 245 g of dithiophosphoric acid-O,O-dimethylester was found to separate as the upper liquid phase. This corresponded to a yield of 97% of the theoretical, based on the ammonium-O,O-dimethyldithiophosphate used. The product had a purity of more than 98%.

| Elementary analysis: | $C_2H_7O_2PS_2$ | |
|---|---|---|
| Found: | P 19.5 % | S 40.9 % |
| Calculated: | P 19.7 % | S 40.5 % |
| Analysis: | | |
| 1) Titration with NaOH: | | 99.4 % |
| 2) Argentometric titration: | | 98.5 % |
| 3) Gaschromatographic analysis of methyl ester after esterification with diazomethane: | | 98.4 % |
| 4) Chromatography in liquid phase: $n_D^{25} = 1.5333$ | | 98.1 % |

EXAMPLE 2

350 g of ammonium-O,O-dimethyl-dithiophosphate was added in manner described in Example 1, within 30 minutes at 25° C and with agitation to 784 g of 75% sulfuric acid. Following this, the whole was thoroughly mixed for a further 30 minutes to complete the reaction. The reaction mixture was delivered to a separating vessel, allowed to stand therein for 10 minutes and the dithiophosporic acid-O,O-dimethylester was separated. 312 g of a liquid upper phase was obtained. This corresponded to a 98.6% yield of dithiophosphoric acid-O,O-dimethylester. In its purity, the product was identical with the dithiophosphoric acid-O,O-dimethylester described in Example 1.

A further minor quantity of dithiophosphoric acid-O,O-dimethylester could be recovered from the lower phase by extracting it with 120 ml of toluene. The ester was isolated by phase separation. The solvent was removed by distillation under mild vacuum and a further 3.8 g of dithiophosphoric acid-O,O-dimethylester was obtained.

The total yield was 99.8%, based on the ammonium-O,O-dimethyldithiophosphate used.

EXAMPLE 3

175 g of ammonium-O,O-dimethyldithiophosphate was reacted in the manner described in Example 1 with the appropriate quantity of 85% $H_3PO_4$ and the dithiophosphoric acid-O,O-dimethylester having a purity of 98.8% was obtained in a yield of 96.8%.

EXAMPLE 4

Ammonium-O,O-dimethyldithiophosphate and 50% sulfuric acid were used in the quantitative ratio of 1 : 2.8 and reacted at 22° C in the manner described in Example 2. During the reaction, the temperature dropped down to 7° C. The whole was allowed to react for a further 10 minutes, delivered to a separating vessel and allowed to remain therein for 10 minutes. After phase separation, dithiophosphoric acid-O,O-dimethylester of 99.4% strength was obtained. The yield was practically quantitative.

EXAMPLE 5

175 g of ammonium-O,O-dimethyldithiophosphate and 250 g of 36.5% hydrochloric acid were reacted for 10 minutes with agitation. During the reaction, the temperature dropped down to 13° C. After filtration, there was obtained 153 g (96.8% of the theoretical) of dithiophosphoric acid-O,O-dimethylester, as the lower phase. The product had a purity of 99.8% and a refractive index $n_D^{25}$ of 1.5333.

EXAMPLE 6

203 g of ammonium-O,O-diethyldithiophosphate was added within 5 minutes with agitation to 485 g of 75% phosphoric acid. The reaction temperature dropped from initially 24° C down to 17° C after a post-reaction period of 10 minutes. The liquid reaction mixture was delivered to a separating vessel. It was allowed to remain therein for 10 minutes and 182.9 g of dithiophosphoric acid-O,O-diethylester was obtained as the upper phase. The yield was 98.2% of the theoretical, based on the ammonium-O,O-diethyldithiophosphate used. The product so made had a purity of 99.9% ($AgNO_3$ and NaOH-values) ($n_D^{25} = 1.5108$).

EXAMPLES 7 AND 8

Ammonium-O,O-diisopropyldithiophosphate and ammonium-O,O-di-n-butyldithiophosphate, respectively, were reacted with 75% phosphoric acid (250% excess) in the manner described in Example 6.

99.3% dithiophosphoric acid-O,O-diisopropyldithiophosphate was obtained in a yield of 98.3%.

Dithiophosphoric acid-O,O-di-n-butyldithiophosphate was obtained in a yield of 97.9%. The purity was substantially 100%.

EXAMPLE 9

63 g of potassium-O,O-diisopropyldithiophosphate was added at 22° C with thorough agitation to 115 g of phosphoric acid of 75% strength. After a post-reaction period of 1 hour, the reaction mixture was delivered to a separating vessel and allowed to remain therein for 30 minutes. 52.2 g of liquid dithiophosphoric acid-O,O-diisopropylester was separated as the upper phase. The product had a purity of 99.1% and was obtained in a yield of 97.6%.

EXAMPLE 10

The procedure was the same as that described in Example 9 save that the potassium dithiophosphate was replaced by sodium-O,O-diisopropyldithiophosphate and that a 300% excess of 80% $H_3PO_4$ was used. Substantially the same result as that described in Example 9 was obtained.

We claim:
1. A process for making pure dithiophosphoric acid-O,O-diesters of the general formula

in which the radicals $R_1$ and $R_2$, being identical or different, each stand for linear and/or branched alkyl, cycloalkyl, alkenyl, alkinyl, aralkyl or aryl radicals having up to 18 carbon atoms, from their salts of the general formula

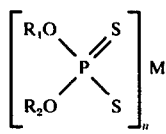
(II)

in which $R_1$ and $R_2$, respectively, have the meanings given hereinabove, M stands for a metal or ammonium cation, and $n$ stands for the valency of the particular cation, which comprises mixing at temperatures within the range $-5°$ and plus $60°$ C the salts with strong mineral acids having a strength within the range 30 and 90 weight % in the quantity necessary to ensure dissolution of the salts and formation of two separate liquid phases, and separating the two phases from one another.

2. The process as claimed in claim 1, wherein sulfuric acid or phosphoric acid is used.

3. The process as claimed in claim 1, wherein the reaction is effected at temperatures within the range $0°$ and $30°$ C.

4. The process as claimed in claim 1, wherein the acids used have a strength within the range 65 and 85 weight %.

5. The process as claimed in claim 1, wherein the acids are used in an excess, based on the theoretical quantity.

6. The process as claimed in claim 1, wherein the dithiophosphate of formula (II) and the acid are used in a quantitative ratio greater than 1:12.

7. The process as claimed in claim 6, wherein the dithiophosphate of formula (II) and the acid are used in a quantitative ratio of 1:5 to 1:1.

8. The process as claimed in claim 1, wherein the starting material is selected from the alkali metal and ammonium salts of dithiophosphoric acid-O,O-diesters.

* * * * *